US00RE34070E

United States Patent [19]

Regimand

[11] E Patent Number: Re. 34,070

[45] Reissued Date of Patent: Sep. 22, 1992

[54] METHOD AND SYSTEM FOR TRANSFERRING CALIBRATION DATA BETWEEN CALIBRATED MEASUREMENT INSTRUMENTS

[75] Inventor: Ali Regimand, Research Triangle Park, N.C.

[73] Assignee: Troxler Electronic Laboratories, Inc., Research Triangle Park, N.C.

[21] Appl. No.: 534,732

[22] Filed: Jun. 7, 1990

Related U.S. Patent Documents

Reissue of:

[64] Patent No.: 4,864,842
Issued: Sep. 12, 1989
Appl. No.: 226,137
Filed: Jul. 29, 1988

[51] Int. Cl.[5] ..... G01D 18/00

[52] U.S. Cl. ..... 73/1 R; 250/252.1; 364/571.02

[58] Field of Search ..... 73/1 R; 364/571.01, 364/571.04, 571.07, 571.05, 571.06, 571.08; 250/390.04, 390.05, 252.1 R, 390.01, 390.06, 390.03, 252.1 A

[56] References Cited

U.S. PATENT DOCUMENTS

| | | | |
|---|---|---|---|
| 2,564,626 | 8/1951 | MacMahon et al. | 250/390.03 X |
| 2,951,200 | 8/1960 | Critchlow | 364/571.01 X |
| 3,492,479 | 1/1970 | Lowery et al. | 250/390.04 |
| 3,519,821 | 7/1970 | Bolster | 250/252.1 R |
| 4,079,237 | 3/1978 | Schlesinger | 364/563 |
| 4,152,600 | 5/1979 | Berry | 250/252.1 R |
| 4,155,009 | 5/1979 | Lieber et al. | 250/308 |
| 4,198,677 | 4/1980 | Brunner et al. | 324/130 X |
| 4,374,326 | 2/1983 | Wykes et al. | 250/252.1 R X |
| 4,571,491 | 2/1986 | Vinegar et al. | 250/252.1 R |
| 4,671,097 | 6/1987 | Kurki et al. | 364/571.04 X |
| 4,873,655 | 10/1989 | Kondraske | 364/571.07 X |
| 4,874,950 | 10/1989 | Regimand | 250/390.04 |

FOREIGN PATENT DOCUMENTS

| | | | |
|---|---|---|---|
| 353118 | 7/1991 | European Pat. Off. . | |
| 2264674 | 1/1975 | Fed. Rep. of Germany | 250/252.1 R |
| 160378 | 6/1983 | German Democratic Rep. | 250/390.05 |
| 135842 | 7/1985 | Japan | 250/252.1 R |
| 240118 | 9/1969 | U.S.S.R. | 250/252.1 R |
| 1008684 | 3/1983 | U.S.S.R. | 250/252.1 R |
| 1093985 | 5/1984 | U.S.S.R. | 250/252.1 R |
| 2072349 | 9/1981 | United Kingdom . | |

OTHER PUBLICATIONS

Troxler Electronic Laboratories, Inc., Brochure on the Troxler 3241 Asphalt Content Gauge, published by Jul. 1988, 2 pages.

Troxler Electronic Laboratories, Inc., Operations Manual for 3241-B Asphalt Content Gauge, 1985, pp. 20-22.

Illinois Department of Transportation Specification, Jan. 1987, pp. 5-6.

*Primary Examiner*—Tom Noland

*Attorney, Agent, or Firm*—Bell, Seltzer, Park & Gibson

[57] ABSTRACT

The present invention provides a method and system which is useful on instruments requiring experimentally determined calibration curves by which calibration data can be transferred to a plurality of field gauges, thereby avoiding the necessity of individually calibrating each gauge each time calibration is necessary. The field gauges are initially cross related to a master gauge. At a later time when a new calibration is necessary, the master gauge is calibrated using carefully prepared samples of a test material. Using the experimentally derived calibration curves with the cross relation data provides calibration data for the field gauges.

27 Claims, 4 Drawing Sheets

METHOD AND SYSTEM FOR TRANSFERRING CALIBRATION DATA BETWEEN CALIBRATED MEASUREMENT INSTRUMENTS

Matter enclosed in heavy brackets [ ] appears in the original patent but forms no part of this reissue specification; matter printed in italics indicates the additions made by reissue.

FIELD OF THE INVENTION

This invention relates to measurement instruments requiring experimentally determined calibration curves, where minor variations in instrument characteristics necessitate individual calibration, and more particularly relates to a method and system which facilitates the calibration of such instruments.

BACKGROUND OF THE INVENTION

Many types of measurement instruments rely upon experimentally determined calibration curves to convert the raw data which is read by the instrument into an accurate measurement reading. Typically, the calibration curve is derived by taking measurement readings with the instrument on several samples whose composition has been determined analytically, and then constructing a calibration curve which relates the experimentally determined measurement readings to the analytically determined composition values. Because of minor variations from one measurement instrument to another, a calibration curve is unique for a particular instrument, and it is therefore necessary for each measurement instrument to be calibrated individually. The present invention provides a method and system which greatly facilitates the calibration procedure. This invention is described herein in terms of the calibration of a neutron gauge designed for measuring the asphalt content of bituminous paving mixes. This invention can, however, be embodied in many different forms and can be used with other types and designs of instruments which employ experimentally derived calibration curves.

Lowery, et al. U.S. Pat. No. 3,492,475 discloses a portable nuclear gauge which utilizes a fast neutron source and a thermal neutron detector for determining the composition of a bulk material, such as a bituminous paving mix, placed in a sample pan. This type of gauge relies upon the neutron moderating characteristics of hydrogen atoms present in the composition for determining, for example, the amount of asphalt in a paving mix or the amount of moisture in a building material. For these determinations it is known that the amount of asphalt or the amount of moisture can be related to the hydrogen content of the material, and the hydrogen content of the material can be determined by subjecting the sample to radiation from a fast neutron source and detecting neutrons which have been slowed or thermalized as a result of interaction with the hydrogen nuclei present in the sample. The number of thermalized neutrons detected (counted) over a period of time is utilized in determining the hydrogen content of the sample.

In operating the gauge, it is first necessary to establish a standard count for calibration purposes. This is accomplished using a standard sample having a known hydrogen content, for example, a block of polyethylene. Then calibration curves are produced for the particular material being tested, by using carefully prepared samples having a known content of the hydrogen-containing material of interest (e.g. asphalt or moisture). After the calibration curves have been produced, unknown test samples can be placed in the gauge and counts are taken. By reference to the calibration curve, the corresponding content of the hydrogen-containing material for that count can be read.

A more recent model of this gauge has been produced by applicant's assignee embodying the principles of the Lowery patent and sold as the "Model 3241 Asphalt Content Gauge" by Troxler Electronic Laboratories, Inc. This gauge includes a microprocessor to facilitate calibration and computation of the sample asphalt content. Calibration can be made by taking gauge counts on two or more samples of known asphalt content. The microprocessor then constructs a calibration equation from these data points, and the gauge provides a direct readout of the percent asphalt, thus eliminating the necessity of calculations and reference to external calibration tables.

In order to obtain the most accurate measurements, the gauge must be calibrated each time the composition of the material is changed. This is because the number of counts recorded is only representative of the hydrogen atoms present in the sample. There is an assumption made when using a thermal neutron gauge that the differences in hydrogen count from sample to sample are because of changes in the amount of the substance of interest, such as moisture or asphalt content, and that all other factors are maintained substantially constant. The calibration is done when it is clear that the "other factors" are not going to be constant. Such changes may occur, for example, when using a new aggregate in the paving mix or a new source or grade of asphalt. A new aggregate may have a different average moisture content or a different intrinsic hydrogen content. In the case of asphalt, different sources of asphalt may have a different concentration of hydrogen. At a time when there is such a change, the gauge must be calibrated using carefully prepared samples of known concentrations of the hydrogen-containing material of interest.

As discussed above, the calibration procedure involves taking hydrogen counts with the gauge using several samples of known composition, and establishing a correlation, (e.g. an equation or a calibration curve) which can be used to obtain a percent asphalt reading from the hydrogen counts obtained from a test sample of unknown composition. The calibration procedure itself is not unduly complex, and is practical with a single gauge or where a relatively few gauges are involved. However, where a number of field gauges are used, as is frequently the case in many operations, the necessity of manually calibrating all the gauges becomes quite burdensome and time consuming. The gauges generally need to be taken out of the field and sent to a lab where samples of the new aggregate can be carefully mixed and tested to get a proper calibration. This involves the inconvenience of the loss of use of the gauges during the time they are being calibrated, and also the inconvenience of having to transport the gauges back and forth from the lab.

With the foregoing in mind, it is an object of the present invention to overcome the problems and disadvantages of the prior practices discussed above and to provide an improved system for calibrating gauges in a simpler and more time efficient manner without having to transport the gauges back to the lab.

SUMMARY OF THE INVENTION

The invention achieves the foregoing and other objects by providing an efficient system by which calibration data can be transferred to a plurality of field gauges, thereby avoiding the necessity of individually calibrating each gauge. The calibration data required by the gauges is obtained by a master gauge typically kept at the lab. This calibration data is easily transferred to the respective field gauges so that the field gauges are permitted to stay in the field.

The process essentially comprises providing a master instrument (e.g. a neutron gauge), and at least one field instrument (e.g. a neutron gauge). Since each instrument has different measurement characteristics, a cross relationship is established between the readings obtained from the master instrument when measuring a particular material and those detected by the field instrument when measuring the same material.

When a calibration is necessary, due to the use of a new material source for example, the conventional manual calibration procedure is carried out in the lab on the master gauge and master calibration constants are established for the particular material. Adjusted calibration constants, specific for a particular field gauge, are created by adjusting the master calibration constants based upon the previously established cross relationship between the master gauge and the particular field gauge. The adjusted calibration constants are used in the field gauge to obtain measurements on the new material.

In accordance with one embodiment of the invention, the field gauges are specially equipped with means for storing the previously derived cross relationship between the master gauge and the field gauge, and means is provided in the field gauge for directly receiving master calibration constants obtained from the master gauge. The gauge is also equipped with means for applying the stored cross relationship to the newly obtained master calibration constants to create adjusted calibration constants specific for the particular field gauge. Thus whenever a calibration is necessary, such as when a new variation of asphalt is used, the master calibration constants are derived in the laboratory by the master gauge, and these newly derived master calibration constants are then distributed to the field gauges in use. The master calibration constants are loaded into each field gauge, and in each field gauge the master calibration data is adjusted based upon the unique cross relationship data which is stored in the field gauge. This is much easier and quicker than requiring individual calibration of each field gauge.

However, the calibration data transfer procedure of this invention can also be utilized in instruments which are not specially equipped for calibration data transfer, such as for example the asphalt content gauges noted earlier, which have been produced by applicant's assignee for many years. For use in these gauges, the master calibration constants are obtained in the laboratory on a master gauge and cross relationships between each field gauge and the master gauge are established in the manner noted above. Then the master calibration constants are adjusted for each field gauge using the previously derived cross relationships for each field gauge. This can be accomplished manually or preferably through the use of a computer. Then the adjusted calibration constants for each gauge are distributed to the respective field gauges and loaded into the appropriate field gauge for use in performing subsequent measurements. This permits the field units to stay in the field and avoids the time consuming process of individually calibrating each field gauge.

BRIEF DESCRIPTION OF THE DRAWINGS

Some of the features and advantages of the invention having been stated, others will become apparent as the description proceeds, and taken in connection with the accompanying drawings, in which.

DETAILED DESCRIPTION OF THE PREFERRED EMBODIMENTS

The present invention will now be described more fully with reference to the drawings, in connection with a particular type of neutron gauge designed for measuring the asphalt content of bituminous paving mixes. This invention can, however, be embodied in many different forms and can be used with other types and designs of instruments which use experimentally determined calibration curves. It should be understood therefore that the specific embodiments described herein are illustrative of how the present invention may be practiced, and that the invention is not limited to these specific embodiments.

Figure 1:
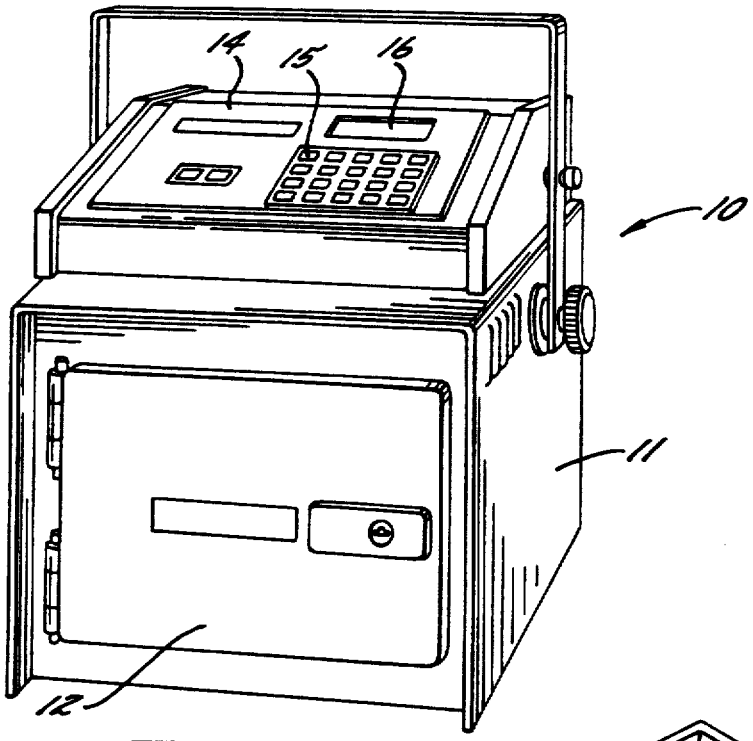
Fig. 1. (PRIOR ART)
FIG. 1 is a perspective view of a neutron gauge.
Figure 2:
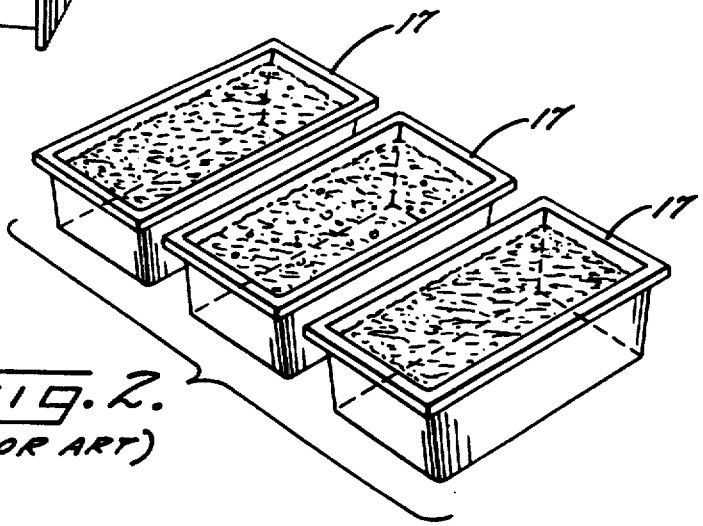
Fig. 2. (PRIOR ART)
FIG. 2 is a perspective view of several sample pans filled with samples to be tested in the neutron gauge.
Figure 3:
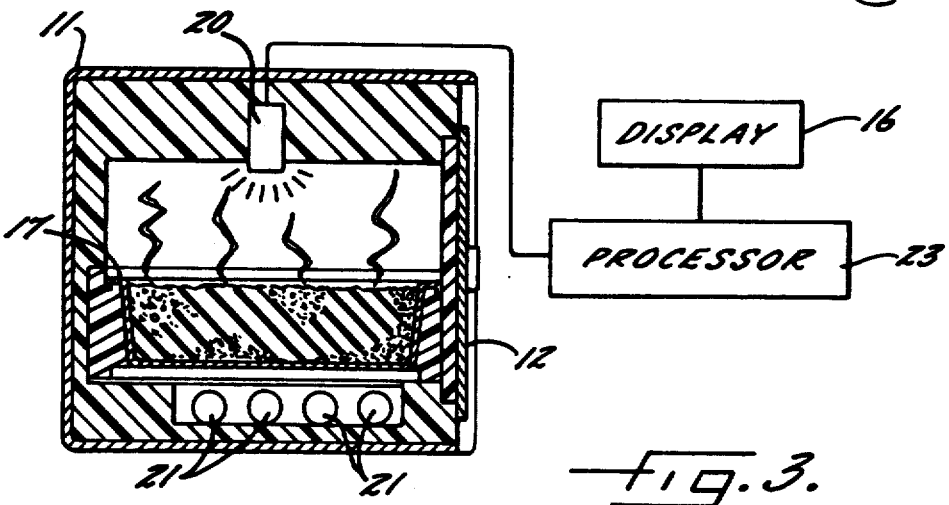
Fig. 3. (PRIOR ART)
FIG. 3 is a front cross section view of the neutron gauge of FIG. 1 illustrating its basic components.

A neutron gauge is generally indicated by the number 10 in FIG. 1 and comprises a generally rectangular housing 11 having a door 12 which provides access to a measurement chamber in which sample pans are placed for measurement. A control unit 14 is provided, including a keypad 15 for entry of data and for controlling the functions of the gauge, and a display 16, which may be of any suitable construction, such as a liquid crystal display. Referring to FIG. 2, there is shown several sample pans 17 containing samples of asphalt-aggregate paving mix. The sample pans are sized to fit into the measurement chamber of the neutron gauge. Referring to FIG. 3, a sample pan 17 is received within the interior of the gauge. Located in the upper interior portion of the gauge is a source 20 of fast neutrons. The source 20 may for example suitably comprise a Am-241:Be source. In the lower interior portion of the gauge beneath the sample pan are a series of detector tubes 21 for detecting neutrons which have been slowed or thermalized by interaction with hydrogen atoms present in the sample. The illustrated detectors 21 are $He^3$ detector tubes but [an] *any* suitable thermal neutron detector will suffice. The gauge also includes a data processor module 23 for controlling the gauge and counting of thermalized neutrons.

To operate the gauge, the sample pan is filled with a sample of material and inserted into the interior of the gauge. The door is shut and fast neutrons from the source 20 are emitted down through the sample in the sample pan 13. Hydrogen present in the sample interacts with the fast neutrons, producing moderated or slowed neutrons, and thermalized neutrons below a specified energy level are detected by detectors 21. The thermalized neutrons are counted for a predetermined period of time and a count is recorded in the data processor module 23. The data processor module 23 then correlates the number of counts to a moisture content or an asphalt content calibration to indicate the result.

Figure 4:
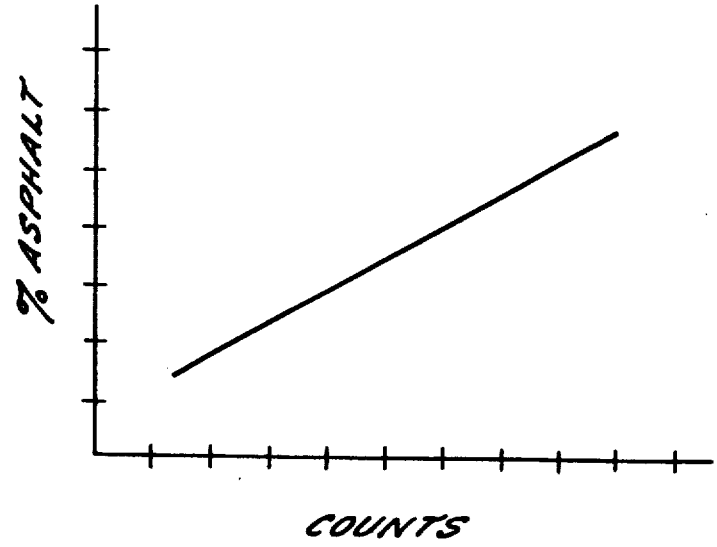
FIG. 4. (PRIOR ART)
FIG. 4 is a graph illustrating the general relationship of thermal neutron counts to the asphalt content of a sample of asphalt-aggregate paving mix and graphically representing the calibration of a thermal neutron gauge.

The correlation between counts and asphalt content is unique for each gauge. This is because each fast neutron source 20 emits neutrons at its own particular rate and the detectors also have variations in efficiency and design from unit to unit. Therefore, each gauge must be calibrated in order that the data processor module 23 can convert the number of counts into a value for the asphalt content of the sample. To calibrate the gauge in accordance with conventional methods known in the art, several samples are carefully prepared with known asphalt contents and are used in the gauge to generate counts. The correlation can be done in several different ways. For example, as shown in FIG. 4 the relationship between observed counts and known asphalt content can be graphed. Then, a linear or other form of equation can be formulated to fit the data. Other ways include the creation of a "look up" table where the various asphalt contents are cross referenced with a number of counts.

Calibration is best and most easily accomplished in the lab. This way, the known sample mixtures can be carefully prepared and the most precise calibration can be obtained. However, if the user has a number of these gauges in use in the field, which is often the case, returning the gauges to a lab each time calibration becomes necessary is most inconvenient and would seriously interfere with the user's operations.

Figure 5:
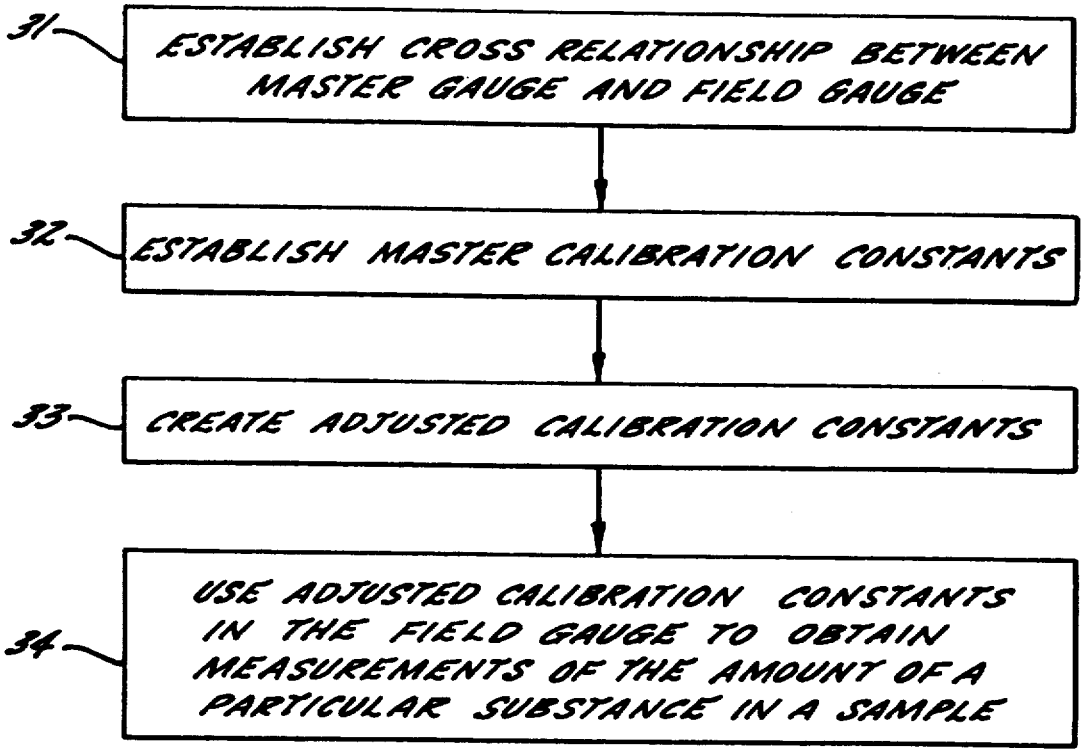
FIG. 5 is a flow chart illustrating the basic procedures followed by the present invention.

The present invention eliminates the necessity of returning field gauges to the lab for calibration by providing a system by which calibration data can be transferred from a lab-based master gauge to one or more field gauges. Illustrated in FIG. 5 is the general process of the system. The first step 31 is to establish a cross relationship which establishes the variance between the thermal neutron counts detected by the master gauge and the counts detected by the field gauge when measuring the same sample. This is accomplished by taking counts on various samples with both the master gauge and the field gauge. The composition of the samples is not critical, although it is desirable that the samples have a hydrogen content generally similar to that of the material which are to be measured during use of the gauge. Most desirably, several samples are used having a hydrogen content which spans the range of measurement of the gauge. For example, standard blocks of solid polyethylene or polyethylene/metal laminates such as that shown in commonly-owned U.S. Pat. No. 4,152,600 may be employed. The second step 32 involves performing a conventional calibration procedure with the use of the lab-based master gauge to obtain master calibration constants. This calibration procedure would be carried out whenever calibration is required, such as due to the use of a new type or variation of paving mix. In order for the master calibration constants to be usable in the field gauge, they must be adjusted or converted to take into account the differences in measurement between the field gauge and the master gauge. As indicated at 33 in FIG. 5, adjusted calibration constants are created by applying the previously derived cross relationship between the master gauge and field gauge to the master calibration constants to thereby obtain adjusted calibration constants specific for the particular field gauge. The final step 34 of the process is to use the adjusted calibration constants in the field gauge on the material to obtain measurements of the amount of the constituent of interest.

In accordance with one embodiment of the present invention, the calibration data transfer procedure is used on gauges which are specially equipped to store the previously defined master gauge/field gauge cross relationship and to receive unmodified calibration constants from the master gauge and to internally adjust the constants based upon the stored master gauge/field gauge cross relationship to produce adjusted calibration constants which are specific for the particular field gauge and which can be used thereafter for determining percent asphalt based upon a thermal neutron count.

For this purpose, the data processor module 23 includes a stored calibration transfer procedure or subroutine which can be called whenever the calibration transfer procedure is to be run. This procedure permits manual entry of the master gauge/field gauge cross relationship by the operator and stores this data in memory for subsequent use. It also permits entry by the operator of the new master calibration constants, either manually or via a suitable transfer media such as magnetic disk or EPROM. Additional data, such as background readings, explained more fully below, can also be entered at this time. After entry of all needed data, the calibration transfer subroutine carries out a mathematical computation to adjust the master calibration constants based upon the stored master gauge/field gauge cross relationship to create adjusted calibration constants which are thereafter stored and used by the field gauge in converting thermal neutron counts into values for percent asphalt. The method and apparatus in accordance with this embodiment of the present invention is advantageous in that the calibration procedure is quite simple and is essentially automated. Since the master gauge/field gauge cross relationship is stored in the field gauge, accuracy is assured in converting or adjusting the master calibration constants to establish adjusted constants for the specific field gauge.

When the calibration data transfer procedure of the present invention is used with conventional thermal neutron gauges which are not specially equipped for receiving and internally storing the master gauge/field gauge cross relationship, the adjustment of the master calibration constants is performed before the calibration data is physically transferred to the field gauge. This may be suitably accomplished at the laboratory either manually or by a computer program which executes a procedure or subroutine similar to that described above. After adjusting the master calibration constants using appropriate master gauge/field gauge cross relationship, the adjusted calibration constants are then physically transferred to the appropriate field gauge. Depending upon the specific gauge and how it is designed to receive calibration data, the entry of the adjusted calibration data into the field gauge may be by manual entry or by other means, such as electronically.

Figure 6:
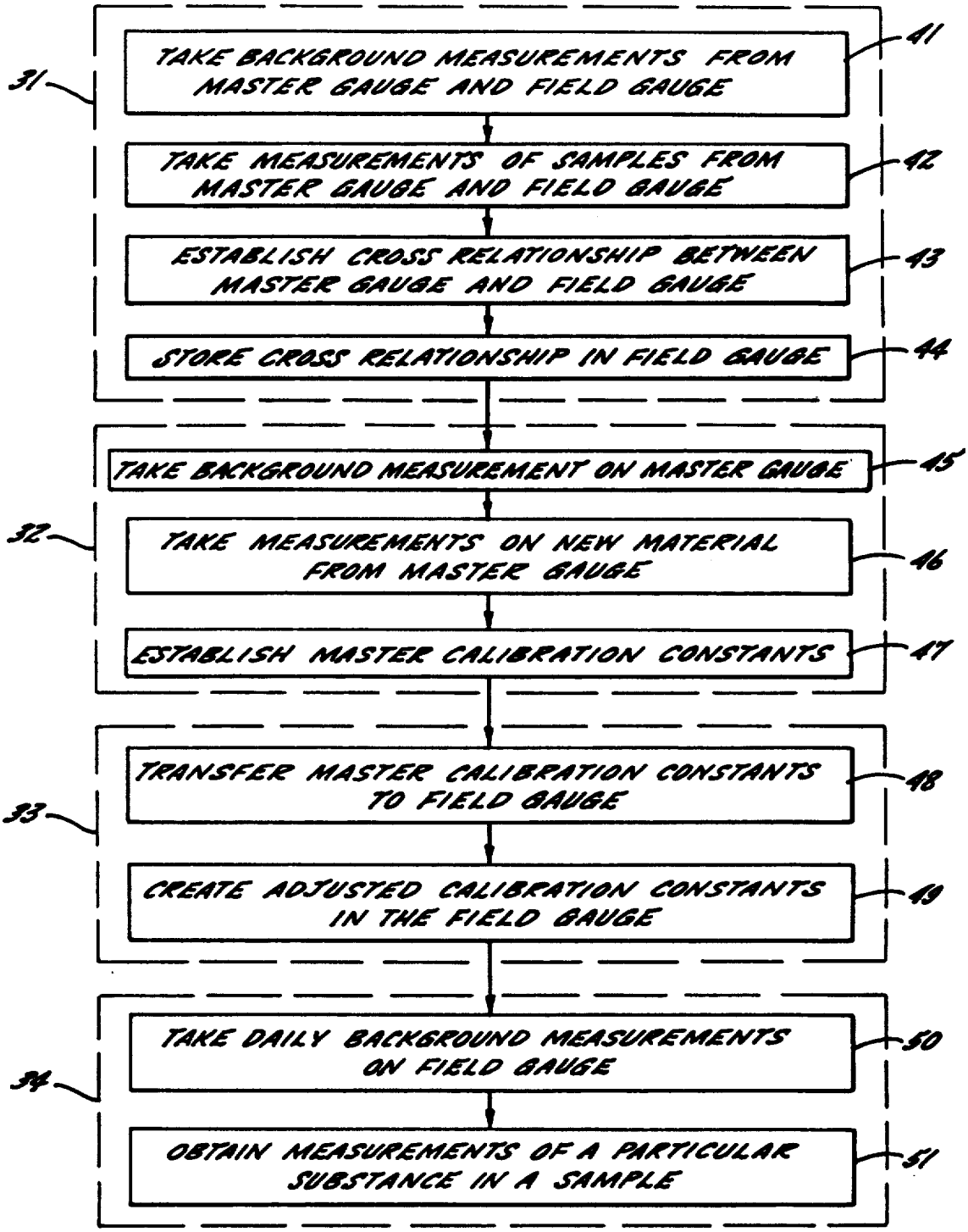
FIG. 6 is a flow diagram illustrating the detailed procedures pursuant to one embodiment of the present invention where specially equipped field gauges are employed.

The procedure in accordance with the first embodiment of the invention is illustrated in more detail in FIG. 6. The broad steps or operations described above with reference to FIG. 5 are shown in the broken line boxes and bear the same reference numbers. The more detailed steps or operations are shown in the solid line boxes. Thus, one step in establishing the master gauge/-field gauge cross relationship includes taking a background reading on each of the master gauge and field gauges, as indicated at 41. The background readings are to eliminate the possible error for the day to day differences in the field and lab conditions and also the changes that occur over time in the source 20. The background reading is made by taking a count without any sample in the gauge. The master gauge original background reading is specified as MOBG and the field gauge original background is specified as FOBG. As earlier discussed, several samples are measured by the master and field gauges as indicated at 42 and a cross relationship is established as indicated at 43. Preferably, the cross relationship is established by selecting a minimum of five samples covering the range of percent asphalt used. The readings from the five samples are recorded as $R_{M1}$, $R_{M2}$, $R_{M3}$, $R_{M4}$, and $R_{M5}$ for the master gauge and $R_{F1}$, $R_{F2}$, $R_{F3}$, [$P_{F4}$] $R_{F4}$, and $R_{F5}$ for the field gauge. A cross relationship between the two gauges can now be established by fitting the counts from one gauge against the other. Please note that only the linear form of this process is considered here, but this procedure can be performed with other equations. Thus, $$R_{Mj}=E_1+E_2R_{Fj}$$

where j=1, 2 . . . 5. The cross relationship, which includes $E_1$, $E_2$, MOBG and FOGB, is stored in the field neutron gauge or more particularly the central processing module 23, as indicated at 44.

At subsequent times, when it is necessary to calibrate a field gauge, which is most often done when a different type or variety of material is used, calibration is performed using the master gauge. The master gauge is used to generate a background count on the empty gauge chamber as indicated at 45. The background count is specified as MBG. The master gauge is then used to test carefully prepared samples of a particular variety of the asphalt-aggregate paving mix, as indicated at 46, and the samples are used to generate master calibration constants as indicated at 47. A minimum of two samples are employed covering the range of asphalt used. This will give readings $R_1$ and $R_2$. The counts $R_1$ and $R_2$ are now used with the known asphalt content samples to establish the master calibration constants $A_1$ and $A_2$, using the relationship $$\%AC=A_1+A_2R_M \quad (1)$$

where $R_M$ is master gauge count and %AC is asphalt content.

The master calibration constants, which include $A_1$, $A_2$ and MBG, are then transferred and input into the field neutron gauge, or more particularly the central processing module 23 as indicated at 48. Then as indicated at 49, the field gauge creates adjusted calibration constants $AA_1$ and $AA_2$ by adjusting the master calibration constants $A_1$ and $A_2$ based on the cross relationship stored in the field gauge.

The following discussion explains how the adjusted calibration constants are derived. Using the equation $$R_M=E_1+E_2R_F \quad (2)$$

to account for any changes in the gauge counts since the time of cross calibration the stored background counts have to be used in the above equation, so $$R_M+(MOBG-MBG)=E_1+E_2[R_F+-(FOBG-DBG)] \quad (3)$$

wherein DBG is the field gauge daily background count. $R_M$ is calculated Master Gauge count, and $R_F$ is the measured Field Gauge Count. Rewriting equation (3)

$$R_M=E_1+E_2[R_F+(FOBG-DBG)]+MBG-MOBG \quad (4)$$

For simplicity let $$F_1=MBG-MOBG$$

and $$R_F^*=R_F+(FOBG-DBG)$$

now $$R_M=E_1+E_2R_F^*+F_1$$

Substitute $R_M$ into equation 1 to get $$\%AC=A_1+A_2(E_1+E_2R_F^*+F_1)$$

$$\%AC=A_1+A_2E_1+A_2E_2R_F^*+A_2F_1$$

or $$\%AC=(A_1+A_2E_1+A_2F_1)+(A_2E_2)R_F^*$$

let $$AA1=A_1+A_2E_1+A_2F_1$$

and $$AA2=A_2E_2$$

Finally, the constants stored in the Field Gauge are AA1 and AA2.

In use, daily background measurements specified as DBG are taken from the field gauge as indicated at 50 and the field gauge is used to obtain measurements of the asphalt content of an asphalt-aggregate paving mix as indicated at 51 such that $$\%AC=AA_1+AA_2(R_F+FOBG-DBG)$$

Figure 7:
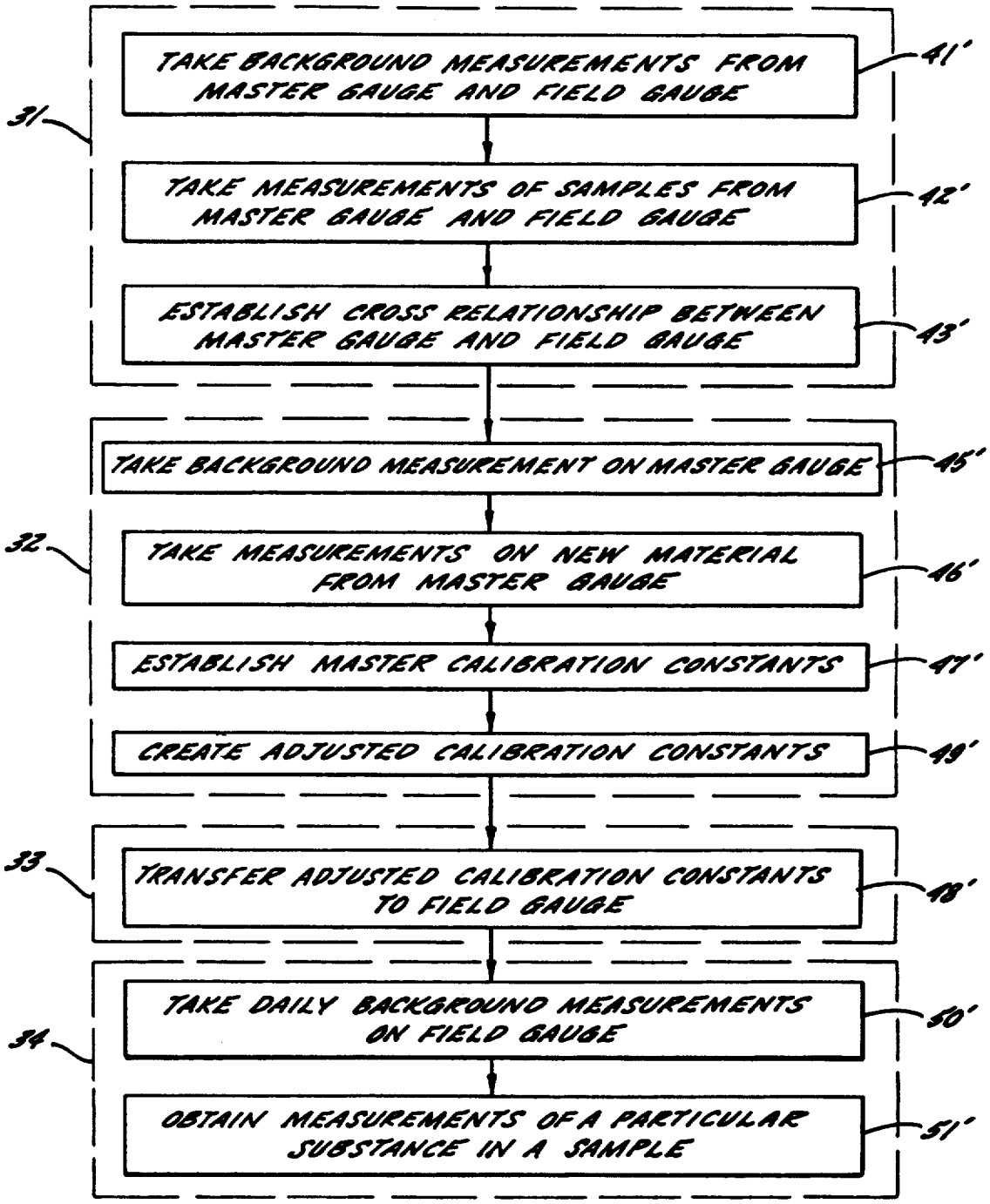
FIG. 7 is a flow diagram similar to FIG. 6 illustrating the detailed procedure of an alternate embodiment of the invention where standard field gauges are employed.

The process of transferring the calibration to the standard gauges is substantially similar to the process described above, and is illustrated in FIG. 7. To avoid repetition, the procedures or steps shown in FIG. 7 which correspond to those previously described in FIG. 6 are identified with corresponding reference characters, with prime notation added. Basically, the fundamental difference in this procedure is that the adjusted calibration constants $AA_1$, $AA_2$ for the field gauge are produced outside of the field gauge (e.g. at the laboratory). Then the adjusted calibration constants $AA_1$, $AA_2$ (rather than the master calibration constants) are transferred to the field gauge as indicated at 48' in FIG. 7.

That which I claim is:

1. A test method for use with measurement instruments of the type which obtain measurement data from a sample and which utilize experimentally determined calibration curves to convert the measurement data into measurement readings, said test method being characterized by facilitating the calibration and use of a number of field instruments, and comprising the steps of providing a master measurement instrument;

providing at least one field measurement instrument;

establishing a cross relationship between the measurement data detected by the master instrument and the measurement data detected by the field instrument;

*obtaining a background measurement by the master instrument;* establishing master calibration data for a particular material by testing samples using the master instrument;

creating adjusted calibration data, specific for a particular field instrument, by adjusting the master calibration data based upon the previously established cross relationship between the master instrument and that particular field instrument *and the previously obtained master instrument background measurement;*

*obtaining a background measurement by the field instrument;* and using the adjusted calibration data in the field instrument *and the background measurement obtained by the field instrument* to convert measurement data obtained by the field instrument into measurement readings.

2. The method according to claim 1, wherein the step of creating adjusted calibration data comprises storing the cross relationship between the master instrument and the field instrument in the field instrument, transferring the calibration data of the master instrument to the field instrument, and applying the stored cross relationship to the master calibration data to create adjusted calibration data in the field instrument for use in converting the measurement data obtained by the field instrument into measurement readings.

3. The method according to claim 1, wherein the step of creating adjusted calibration data comprises applying the previously established cross relationship between the master instrument and the field instrument to the master calibration data to create the adjusted calibration data, transferring the thus created adjusted calibration data to the field instrument, and storing the adjusted calibration data in the field instrument for use in converting the measurement data obtained by the field instrument into measurement readings.

4. The method according to claim 1, wherein the step of establishing a cross relationship between the master instrument and the field instrument comprises obtaining measurement data for a plurality of samples using the master instrument, obtaining measurement data for the same plurality of samples using the field instrument, and defining a relationship between the measurement data obtained by the field instrument and the measurement data obtained by the master instrument; and wherein said step of creating adjusted calibration data comprises applying the thus defined relationship to the master calibration data to thereby derive the adjusted calibration data for the field instrument.

5. A test method for use with nuclear gauges of the type which measure the neutron moderating characteristics of a sample by detecting thermal neutron counts, and through the use of calibration constants for a particular type of material, provide a measurement of the amount of a hydrogenous substance in a sample of the material, said test method being characterized by facilitating the calibration and use of a number of field gauges, and comprising the steps of providing a master neutron gauge;

providing at least one field neutron gauge;

establishing a cross relationship between the thermal neutron counts detected by the master gauge and those detected by the field gauge;

*obtaining a background measurement by the master gauge;* establishing master calibration constants for a particular material using the master gauge;

creating adjusted calibration constants, specific for a particular field gauge by adjusting the master calibration constants based upon the previously established cross relationship between the master gauge and that particular field gauge *and the previously obtained master gauge background measurement;*

*obtaining a background measurement by the field gauge;* and using the adjusted calibration constants in the field gauge *and the background measurement obtained by the field gauge* to obtain measurements of the amount of the hydrogenous substance in a sample of the material.

6. The method according to claim 5, wherein the step creating adjusted calibration constants comprises storing the cross relationship between the master gauge and the field gauge in the field gauge, transferring the calibration constants of the master gauge to the field gauge, and applying the stored cross relationship to the master calibration constants to create adjusted calibration constants in the field gauge for use in obtaining measurements of the amount of said hydrogenous substance in a sample of material.

7. The method according to claim 5, wherein the step of creating adjusted calibration constants comprises applying the previously established cross relationship between the master gauge and the field gauge to the master calibration constants to create the adjusted calibration constants, transferring the thus created adjusted calibration constants to the field gauge, and storing the adjusted calibration constants in the field gauge for use in obtaining measurements of the amount of said hydrogenous substance in a sample of material.

8. The method according to claim 5, wherein the step of establishing a cross relationship between the master gauge and the field gauge comprises obtaining measurements of a plurality of samples by the master gauge, obtaining measurements of the same plurality of samples by the field gauge, and defining a relationship between the measurements obtained by the field gauge and those obtained by the master gauge; and wherein said step of creating adjusted calibration constants comprises applying the thus defined relationship to the master calibration constants generated on the master gauge to thereby derive the adjusted calibration constants for the field gauge.

9. The method according to claim 5, wherein said step of establishing a cross relationship includes the step of establishing an initial background measurement by each of the master gauge and field gauge [and further wherein said step of establishing calibration constants includes obtaining a subsequent background measurement by the master gauge and said step of creating adjusted calibration constants also includes obtaining a subsequent background measurement by the field gauge].

10. A test method for measuring the asphalt content of an asphalt-aggregate paving mix with the use of nuclear gauges of the type which measure the neutron moderating characteristics of a sample of the asphalt-aggregate mix and obtain thermal neutron counts which represent, through the use of calibration constants, a measurement of the asphalt content of a sample of the asphalt-aggregate mix, said method characterized by facilitating the calibration and use of a number of field gauges and comprising the steps of providing a master neutron gauge;

providing at least one field neutron gauge;

*establishing initial background measurements by the master gauge and by the at least one field gauge;* establishing a cross relationship between the thermal neutron counts detected by the master gauge and those detected by the field gauge when measuring the asphalt content of a sample;

*obtaining a subsequent background measurement by the master gauge for use in comparison against the initial master gauge background measurement to adjust for changes in counts since establishment of said cross relationship;* establishing master calibration constants for a particular variety of asphalt-aggregate paving mix using the master gauge;

generating adjusted calibration constants for the particular variety of asphalt-aggregate paving mix which are specific for a particular field gauge by adjusting the master calibration constants based upon the previously established cross relationship between the master gauge and that particular field gauge *and the previously established initial master gauge background measurement;*

*obtaining a subsequent background measurement by the field gauge; and* using the adjusted calibration constants in the field gauge *and the initial and subsequent background measurement obtained by the field gauge* to obtain measurements of the asphalt content of the particular variety of asphalt-aggregate paving mix.

11. The method according to claim 10, wherein the step of generating adjusted calibration constants comprises storing the cross relationship between the master gauge and the field gauge in the field gauge, transferring the calibration constants of the master gauge to the field gauge, applying the stored cross relationship to the master calibration constants to create adjusted calibration constants in the field gauge, and storing the thus created adjusted calibration constants in the field gauge for use in obtaining measurements of the asphalt content of a sample of the asphalt-aggregate paving mix.

12. The method according to claim 10, wherein the step of generating adjusted calibration constants comprises applying the previously established cross relationship between the master gauge and the field gauge to the master calibration constants to generate the adjusted calibration constants, transferring the thus generated adjusted calibration constants to the field gauge, and storing the adjusted calibration constants in the field gauge for use in obtaining measurements of the asphalt content in an asphalt-aggregate paving mix.

13. The method according to claim 10, wherein the step of establishing master calibration constants for a particular variety of asphalt-aggregate paving mix comprises using the master gauge to obtain thermal neutron counts for a plurality of samples of the paving mix having known asphalt contents.

14. A test method for measuring the asphalt content of an asphalt-aggregate paving mix with the use of nuclear gauges of the type which measure the neutron moderating characteristics of a sample of the asphalt-aggregate paving mix by detecting thermal neutron counts, wherein the gauges are calibrated through the use of calibration constants for a particular variety of asphalt-aggregate paving mix and the gauges provide a measurement indicative of the asphalt content in a sample of the particular variety of paving mix, said method being characterized by facilitating the calibration and simultaneous use of a number of field gauges, and comprising the steps of providing a [lab based] master neutron gauge;

providing at least one field neutron gauge;

establishing a cross relationship between the thermal neutron counts detected by a master gauge and those detected by the field *gauge* by obtaining a background thermal neutron count by the master gauge and thermal neutron counts of a plurality of samples of different compositions by the master gauge, also obtaining a background thermal neutron count by the field gauge and thermal neutron counts of the same plurality of samples, and defining the cross relationship between the thermal neutron counts obtained by the master gauge and those obtained by the field gauge;

storing the thus established cross relationship in the field gauge;

establishing master calibration constants for a particular variety of the asphalt-aggregate mix by using the master gauge to obtain thermal neutron counts for samples of known asphalt content;

establishing a master background measurement on the master gauge;

transferring the master calibration constants and the master background measurement to the field gauge;

generating adjusted calibration constants for the particular variety of asphalt-aggregate paving mix which are specific for the particular field gauge by adjusting the master calibration constants based upon the cross relationship which is stored in the field gauge, and using the adjusted calibration constants in the field gauge to obtain measurements of the asphalt content of the particular asphalt-aggregate paving mix.

15. A test method for measuring the asphalt content of an asphalt-aggregate paving mix with the use of nuclear gauges of the type which measure the neutron moderating characteristics of a sample of the asphalt-aggregate paving mix by detecting thermal neutron counts, wherein the gauges are calibrated through the use of calibration constants for a particular variety of asphalt-aggregate paving mix and the gauges provide a measurement indicative of the asphalt content in a sample of the particular variety of paving mix, said method being characterized by facilitating the calibration and simultaneous use of a number of field gauges, and comprising the steps of providing a [lab based] master neutron gauge;

providing at least one field neutron gauge;

establishing a cross relationship between the thermal neutron counts detected by a master gauge and those detected by the field *gauge* by obtaining a background thermal neutron count using the master gauge and thermal neutron counts of a plurality of samples of different compositions by the master gauge, also obtaining a background thermal neutron count using the field gauge and thermal neutron counts of the same plurality of samples using the field gauge, and defining the cross relationship between the measurements obtained by the master gauge and those obtained by the field gauge;

storing the thus established cross relationship;

establishing master calibration constants for a particular variety of the asphalt-aggregate mix by using the master gauge to obtain thermal neutron counts for samples of known asphalt content;

establishing a master background measurement on the master gauge;

generating adjusted calibration constants for the particular variety of asphalt-aggregate paving mix which are specific for the particular field gauge by adjusting the master calibration constants based upon the cross relationship;

transferring the adjusted calibration constants to the field gauge; and using the adjusted calibration constants in the field gauge to obtain measurements of the asphalt content of the particular asphalt-aggregate paving mix.

16. A test system for measurement instruments of the type which obtain measurement data from a sample and which utilize experimentally determined calibration curves to convert the measurement data into measurement readings, said test system being characterized by facilitating the calibration and use of a number of field instruments, and comprising a master measurement instrument;

at least one field measurement instrument;

means for storing a derived cross relationship between the measurement data detected by the master instrument and the measurement data detected by the field instrument;

means for storing master calibration data derived from [tests] *measurements* with the master measurement instrument on a particular material;

means for applying the stored cross relationship to the stored master calibration data to create adjusted calibration data; and means in the particular field instrument for using the adjusted calibration data in the field instrument *and a background measurement made by the field instrument* to convert measurement data obtained by the field instrument into measurement readings.

17. The system according to claim 16, wherein the means for using the adjusted calibration data also includes means for storing the cross relationship between the master instrument and the field instrument and for receiving the recorded master calibration data and for receiving the adjusted calibration data.

18. The system according to claim 16, wherein the means for storing and using the adjusted calibration constants also includes means for receiving the adjusted calibration data.

19. The system according to claim 16, further including means for recording measurement data by the master instrument for a plurality of samples;

means for recording measurement data by the field instrument for the same plurality of samples; and means for deriving a cross relationship between the measurement data obtained by the master instrument and the measurement data obtained by the field instrument.

20. A test system for nuclear gauges of the type which measure the neutron moderating characteristics of a sample, and through the use of calibration constants determined for each particular material a gauge may provide a measurement of the amount of a hydrogenous constituent in a sample of the material, wherein the calibration of a plurality of field gauges is facilitated by the system comprising a master neutron gauge;

at least one field neutron gauge;

means for storing a derived cross relationship between a field gauge and a master gauge defining the variance between the thermal neutron counts detected by the master gauge those detected by the field gauge [between the gauges] for a sample;

means for storing [derived] master calibration constants *derived from measurements with the master gauge* for a particular material;

means for applying the stored cross relationship to the stored master calibration constants to create adjusted calibration constants; and means in the particular field gauge for [storing and] using *the thus created* adjusted calibration constants *and a background measurement made by the field gauge* to measure the amount of a hydrogenous constituent in a sample of the particular material.

21. The system according to claim 20, wherein the means for storing and using the adjusted calibration constants also includes means for storing the cross relationship between the measurements by the master gauge and those by the field gauge and for receiving the recorded master calibration constants and for deriving the adjusted calibration constants.

22. The system according to claim 20, wherein the means for storing and using the adjusted calibration constants also includes means for receiving the adjusted calibration constants.

23. The system according to claim 20, further including means for recording thermal neutron counts by the master gauge for a plurality of samples;

means for recording thermal neutron counts by the field gauge for the same plurality of samples;

means for deriving a cross relationship between the thermal neutron counts detected by the master gauge and those detected by the field gauge.

24. A test system for nuclear gauges of the type which measure the neutron moderating characteristics of a sample of an asphalt-aggregate paving mix, and through the use of calibration constants determined for each particular asphalt-aggregate paving mix a gauge may provide a measurement of the asphalt content of a sample of the asphalt-aggregate paving mix, wherein the calibration of a plurality of field gauges is facilitated by the system comprising a master neutron gauge;

at least one field neutron gauge;

means for recording derived master calibration constants for a particular asphalt-aggregate paving mix;

means in the particular field gauge for storing a cross relationship between the thermal neutron counts detected by the master gauge and those detected by the field gauge;

means in the particular field gauge for receiving the recorded master calibration constants and for applying the stored cross relationship to the master calibration constants to create adjusted calibration constants; and means in the particular field gauge for using the thus-derived adjusted calibration constants to measure the asphalt content in a sample of the particular asphalt-aggregate paving mix.

25. A test system for nuclear gauges of the type which measure the neutron moderating characteristics of a sample of an asphalt-aggregate paving mix, and through the use of calibration constants determined for each particular variety of asphalt-aggregate paving mix a gauge may provide a measurement of the asphalt content of a sample of the asphalt-aggregate paving mix, wherein the calibration of a plurality of field gauges is facilitated by the system comprising a master neutron gauge;

at least one field neutron gauge;

means for storing a derived cross relationship between the thermal neutron counts detected by the master gauge and those *detected* by [each] *a* field gauge *based upon measurements of samples by the master gauge and the field gauge;* means for storing derived master calibration constants for a particular asphalt-aggregate paving mix *based upon measurements by the master gauge of samples of the particular asphalt-aggregate paving mix;* means for applying the stored cross relationship to the stored master calibration constants to create adjusted calibration constants; and means in the particular field gauge for receiving, storing and using adjusted calibration constants *and a background measurement made by the field gauge* to measure the asphalt content in a sample of the particular asphalt-aggregate paving mix.

*26. A test method for use with nuclear gauges of the type which measure the neutron moderating characteristics of a sample by detecting thermal neutron counts, and through the use of calibration constants for a particular type of material, provide a measurement of the amount of a hydrogenous substance in a sample of the material, said test method being characterized by facilitating the calibration and use of a number of field gauges, and comprising the steps of*

*providing a master neutron gauge;*

*providing at least one field neutron gauge;*

*establishing a cross relationship between the thermal neutron counts detected by the master gauge and those detected by a particular field gauge;*

*storing in the particular field gauge the thus established cross relationship between the master gauge and the particular field gauge;*

*establishing master calibration constants for a particular material using the master gauge;*

*transferring the thus established master calibration constants for the particular material to the field gauge;*

*applying the cross relationship stored in the field gauge to the thus transferred master calibration constants to create adjusted calibration constants in the field gauge specific for the particular field gauge; and*

*using the adjusted calibration constants in the field gauge to obtain measurements of the amount of the hydrogenous substance in a sample of the material.*

*27. A test method for measuring the asphalt content of an asphalt-aggregate paving mix with the use of nuclear gauges of the type which measure the neutron moderating characteristics of a sample of the asphalt-aggregate paving mix and obtain thermal neutron counts which represent, through the use of calibration constants, a measurement of the asphalt content of a sample of the asphalt-aggregate paving mix, said test method being characterized by facilitating the calibration and use of a number of field gauges, and comprising the steps of*

*providing a master neutron gauge;*

*providing at least one field neutron gauge;*

*establishing a cross relationship between the thermal neutron counts detected by the master gauge and those detected by a particular field gauge when measuring the asphalt content of a sample;*

*storing in the particular field gauge, the thus established cross relationship between the master gauge and the particular field gauge;*

*establishing master calibration constants for a particular asphalt-aggregate paving mix using the master gauge;*

*transferring the thus established master calibration constants for the particular paving mix to the field gauge;*

*applying the cross relationship stored in the field gauge to the thus transferred master calibration constants to create adjusted calibration constants in the field gauge specific for the particular field gauge;*

*storing the adjusted calibration constants in the field gauge; and*

*using the adjusted calibration constants in the field gauge to obtain measurements of the asphalt content in a sample of the particular asphalt-aggregate paving mix.*

* * * * *

UNITED STATES PATENT AND TRADEMARK OFFICE

CERTIFICATE OF CORRECTION

PATENT NO. : Re. 34,070

DATED : September 22, 1992

INVENTOR(S) : Ali Regimand

It is certified that error appears in the above-identified patent and that said Letters Patent is hereby corrected as shown below:

Column 7, line 34, "FOGB" should be -- FOBG --.

Column 8, line 9, "wherein" should be -- where --.

Column 10, line 30, -- of -- should be inserted after "step".

Column 13, line 4, "by" should be -- using --.

Column 13, line 58, "receiving" should be -- deriving --.

Signed and Sealed this

Nineteenth Day of October, 1993

*Attest:*

Bruce Lehman

BRUCE LEHMAN

*Attesting Officer*

*Commissioner of Patents and Trademarks*